United States Patent [19]
Russo

[11] Patent Number: 5,484,420
[45] Date of Patent: Jan. 16, 1996

[54] RETENTION BOLSTERS FOR PERCUTANEOUS CATHETERS

[75] Inventor: Ronald D. Russo, Barrington, R.I.

[73] Assignee: Wilson-Cook Medical Inc., Winston-Salem, N.C.

[21] Appl. No.: 163,843

[22] Filed: Dec. 7, 1993

Related U.S. Application Data

[63] Continuation-in-part of Ser. No. 911,171, Jul. 9, 1992, Pat. No. 5,267,968.

[51] Int. Cl.$^6$ ................................................ A61M 5/32
[52] U.S. Cl. ...................................... 604/178; 604/174
[58] Field of Search .................................. 604/174, 177, 604/178, 179, 250

[56] References Cited

U.S. PATENT DOCUMENTS

| | | | |
|---|---|---|---|
| 1,696,763 | 12/1928 | Hare | 604/179 |
| 3,444,861 | 5/1969 | Schulte | 604/175 X |
| 3,976,080 | 8/1976 | Bornhorst et al. | 604/179 |
| 4,645,492 | 2/1987 | Weeks | 604/174 |
| 5,188,609 | 2/1993 | Bayless et al. | 604/174 X |
| 5,308,325 | 5/1994 | Quinn et al. | 604/174 X |

*Primary Examiner*—Robert P. Swiatek
*Attorney, Agent, or Firm*—Woodard, Emhardt, Naughton, Moriarty & McNett

[57] ABSTRACT

Retention bolsters for a percutaneous catheter which have a convexly curved exterior surface which contacts the epidermal surface of a patient, and which also provide protection against the catheter kinking. The retention bolsters slide over a catheter until contacting the skin of the patient at the catheter exit site. When secured in place, the bolsters rock along contacting portions between their convexly curved surface and the epidermal surface of the patient in response to movement of the catheter about the exit site, thereby alleviating the added pressure that would otherwise be applied by this movement. Upon the release of lateral pressure against the catheter device, the bolsters return to their original upright position. One bolster incorporates an elongated collar which is flexibly resilient to supportively allow the catheter to be laterally bent away from the exit site without kinking. A removable twist lock is placed around the collar portion of the bolster to securely lock the bolster to the catheter and can also be easily disengaged if the user desires to adjust the bolster or temporarily loosen it so that the surface underneath the bolster can be cleaned. A second bolster prevents kinking of the bolster by means of a curved passageway therein which orients the catheter toward a side exit which is substantially parallel to the skin surface. The side exit bolster also facilitates attachment by means of a slit therein which allows the bolster to be easily advanced over the catheter and pivoted into position thereon.

5 Claims, 6 Drawing Sheets

RETENTION BOLSTERS FOR PERCUTANEOUS CATHETERS

REFERENCE TO RELATED APPLICATION AND INCORPORATION BY REFERENCE

This application is a continuation-in-part of U.S. patent application Ser. No. 07/911,171, now U.S. Pat. No. 5,267,968, filed on Jul. 9, 1992 by the same inventive entity, and entitled A RETENTION BOLSTER FOR PERCUTANEOUS CATHETERS, the complete disclosure of which is hereby incorporated by reference.

BACKGROUND OF THE INVENTION

This invention relates generally to medical devices and, more particularly, to retention bolsters for adjustably supporting a tubular medical device adjacent an epidermal surface.

Typically, a retention bolster is positioned at the exit site of a catheter to hold the catheter securely against the patient's body. The bolster is locked in place to maintain support of the catheter and prevent bending or crimping of the catheter at the exit site. So positioned, bolsters apply continual, direct pressure to the skin at the exit site of the catheter from the patient's body, sometimes having the effect of inhibiting the healing of the skin at the exit site of the catheter and possibly causing necrosis due to the applied pressure.

Bolsters for supporting tubular medical devices, such as catheters, outside the body have generally focused on maintaining the secure anchoring of the device to the patient. To provide lateral support, bolsters have employed flanges, cross-bars, or discs for contacting the epidermal surface. Prior attempts at minimizing the continual, direct pressure applied by these supports have included the placement of pads or webs underneath the cross-bars, for example, of the bolster. Pads and webs, however, have actually tended to increase the localized pressure at the exit site, especially when the catheter, either accidentally or intentionally, is moved thereabout. Further, as percutaneous catheter placement techniques have become increasingly common, catheters have been increasingly used for longer periods of time. As such, infections of the skin at the catheter exit site have become increasingly common as well.

One particular application magnifying the deficiencies of existing bolsters involves the use of percutaneous gastrostomy catheters (PEG tubes) to provide long term access into the stomach. A PEG tube is maintained at its stoma exit site by a retention bolster for several months while it is used to provide access into the stomach. Existing bolsters, however, which remain inflexibly clamped to maintain the catheter in position during use, do not accommodate the unavoidable movements of the catheter during this long period of time. As the catheter is moved about, either accidentally or as it is handled by attending medical personnel, additional pressure is often applied causing the bolster to dig into the skin surface and resulting in pressure sores and maceration of the stoma site. As a result of these deficiencies, existing bolsters have often been the source of irritation and infections of the skin.

A need, therefore, has existed for an improved retention bolster for use adjacent an epidermal surface to support a tubular medical device. Such a bolster, which securely holds a catheter in place while exerting minimal amounts of pressure at the catheter exit site, and permits movement of the catheter about the stoma exit site without causing or aggravating injury thereat, has been disclosed and claimed in the above co-pending application Ser. No. 07/911,171.

Most of the catheters used in long term enteral feeding are made from inert, biocompatible medical grade silicone rubber or polyurethane. These catheters are soft, flexible and are comfortable for the patient. One problem with these catheters has been their tendency to kink at the point where the catheter is flexed over at a right angle, which is often done when the catheter is taped down on the skin surface. Repeated flexing of the catheter at the juncture as it exits the bolster creates continuous stress at that flexure point, such that it weakens the catheter and creates stress fractures and cracking of the catheter wall leading to premature failure of the medical device. This is especially true in smaller diameter size catheters typically 18 Fr. in size or smaller used in pediatric patients. These smaller size catheters have thinner wall thicknesses which makes them even more susceptible to premature failure from repeated flexing of the tube.

SUMMARY OF THE INVENTION

The present invention provides retention bolsters which securely and safely support a percutaneous catheter, or similar device, against an epidermal surface, and allow for movement of the catheter about its exit site without causing or aggravating injury to the patient. The retention bolsters include means for securely attaching to the catheter, and a convexly curved surface for contacting the epidermal surface of the patient. The bolsters attach to the catheter with the convexly curved surface contacting the epidermal surface of the patient, and rock along contacting portions between the convexly curved surface and the epidermal surface in response to movement of the tubular medical device about its exit site. In this way, a rocking movement about the stoma exit site is permitted without causing or aggravating injury thereat. Upon the release of lateral pressure against the catheter device, the bolsters return to their original upright position.

Two preferred embodiments are disclosed herein which, in addition to providing for the secure attachment of a percutaneous catheter as described above, help to prevent the catheter from kinking when it is bent away from the exit site. The first such embodiment incorporates an elongated collar which is flexibly resilient to supportively allow the catheter to be bent therein laterally away from the exit site without kinking. The use of a removable plastic twist lock around the collar portion of the bolster is also provided which securely locks the bolster to the catheter, and can also be easily disengaged if the user desires to adjust the bolster or temporarily loosen it so that the surface underneath the bolster can be cleaned.

The second preferred embodiment prevents kinking of the catheter by means of a curved passageway therein which positions and orients the catheter towards a side exit which is substantially parallel to the skin surface. The side exit bolster also facilitates attachment by means of a slit which allows the bolster to be easily advanced over the catheter and then pivoted into position thereon.

Accordingly, it is an object of the present invention to provide a rockable retention bolster which prevents kinking of the catheter when the catheter is laterally flexed away from its stoma site.

Another object is to prevent premature cracking or fracture of the catheter after repeated positioning of the catheter.

Another object is to provide a convenient and simple means for locking and unlocking the bolster to the catheter.

Another object is to provide for easy adjustment of the bolster and repositioning if desired.

It is a further object of the present invention to provide a rockable retention bolster which holds the catheter fixed at an angle laterally away from the stoma exit site.

Another object is to provide a rockable retention bolster which holds the catheter substantially parallel to the skin surface making it especially useful for active pediatric patients who have long term feeding tube catheters.

It is a further object of the present invention to provide such a bolster which can be easily advanced about a catheter and positioned thereon.

These and other objects and advantages will become apparent from a review of the following specification and claims.

BRIEF DESCRIPTION OF THE DRAWINGS

FIGS. 4a–d are various views of a side exit retention bolster.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
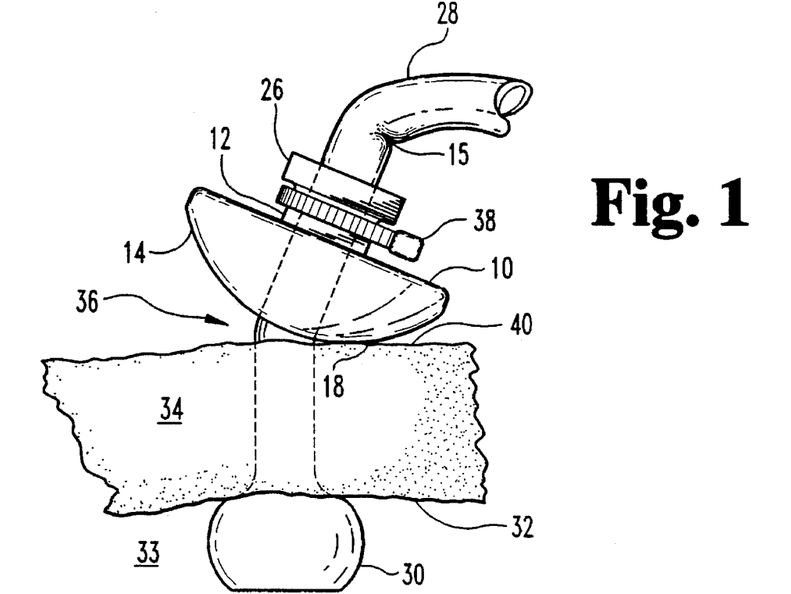
FIG. 1 is a side elevational view of a rockable retention bolster, as disclosed in co-pending application Ser. No. 07/911,171, mounted onto a thin-walled catheter at a stoma site, with the catheter shown kinked from being flexed at an angle away from the bolster.

Referring now to FIG. 1, retention bolster 10 is shown cooperating with a percutaneous gastrostomy catheter 28 having an expanded distal tip 30 for contacting stomach wall or lining 32 of stomach 33. Catheter 28 is maintained clamped across epidermal layer 34 by the compressive action between retention bolster 10 and expanded distal tip 30. As such, expanded distal tip 30 exerts a uniform pressure on stomach wall 32 to maintain a seal therebetween and ensure rapid healing. Similarly, retention bolster 10 exerts an equal and opposite pressure at stoma exit site 36 necessary to maintain the compressive action.

As shown in FIG. 1, retention bolster 10 includes an adjustable clamp 38 about cylindrical portion 12. Clamp 38 adjusts to tighten about cylindrical portion 12 to both clamp and seal catheter 28 within bore 16. As such, retention bolster 10 is held in place contacting the epidermal surface 40. In the orientation shown in FIG. 1, catheter 28 is shown rocked about the stoma exit site along convex surface 18 and epidermal surface 40 in response to movement of the catheter. As an external force is applied to the catheter, such as by positioning the catheter to introduce nutritional liquids into the stomach via the catheter, retention bolster 10 rocks to reduce the pressure on epidermal surface 40 and to move its point of application on the epidermal surface. Because the center of the compressive action between the retention bolster and the expanding tip is shifted away from the exit site, an overturning moment is created which acts to center the catheter once the external force is removed. As such, retention bolster 10 is self-centering. Further, by being self-centering in returning catheter 28 to its normal orientation, retention bolster 10 acts to minimize inward migration of the expanded distal tip 30 into the stomach wall 32.

Figure 2:
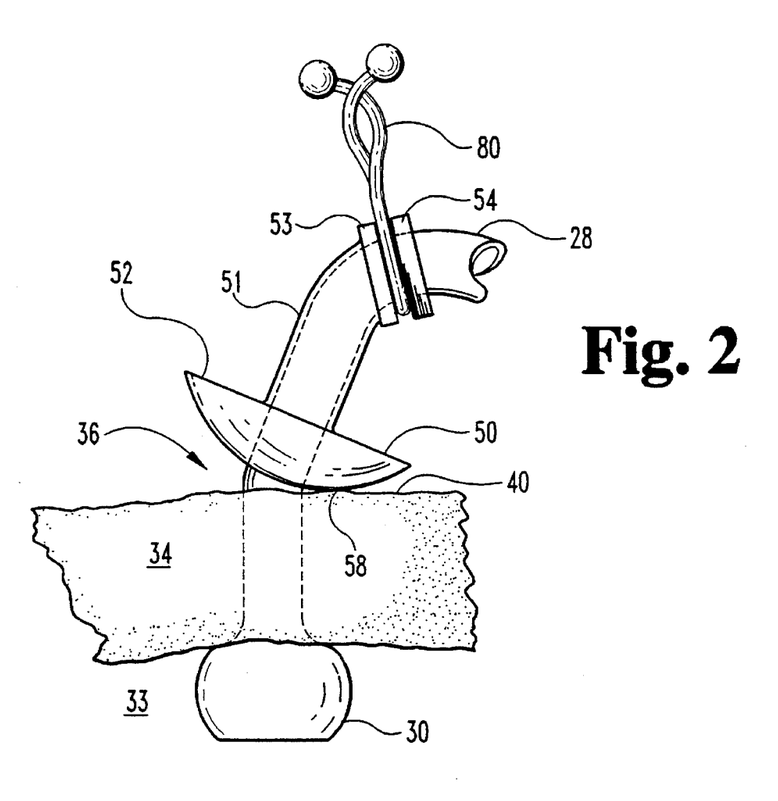
FIG. 2 is a side elevational view of a modified retention bolster with an elongated flexible collar mounted onto a thin-walled catheter at a stoma site, with the catheter shown being flexed at an angle away from the bolster without kinking and being supported by the flexible collar of the bolster.

FIG. 1 shows retention bolster 10, as disclosed in co-pending application Ser. No. 07/911,171, mounted onto thin-walled catheter 28 at stoma site 36, with catheter 28 shown kinked from being laterally flexed away from stoma site 36. In this embodiment, cylindrical portion 12 of bolster 11 has a wall thickness of about 0.100", and a height of about ⅜". Owing to its relative height and thickness, cylindrical portion 12 tends to be more rigid than thin-walled catheter 28. When catheter 28 is thus flexed, as shown in FIG. 1, catheter 28 tends to kink at point 15. This tendency is removed by the following two described new embodiments of the present invention:

FIG. 2 shows a modified retention bolster 50 with an elongated flexible collar 51 that is mounted onto thin-walled catheter 28 at stoma site 36. In FIG. 2, catheter 28 is shown being laterally flexed away from stoma site 36 without kinking, owing to the flexing support that is provided by elongated flexible collar 51. Flexible collar 51 is relatively thin-walled (about 0.03") and elongated (about ¾" in height), which causes collar 51 to act as a flexible support for catheter 28 during flexure to prevent catheter 28 from kinking. Collar 51 thus serves as a strain relief which eliminates kinking or premature stress cracking of catheter 28. When catheter 28 is thus flexed laterally away from stoma site 36, the convexly curved underside contacting portion 58 of bolster 50 rocks and flexible collar 51 bends to thus cooperatively serve to avoid strain from being placed on catheter 28 during flexure. This simple yet functional reconfiguration has resulted in an excellent benefit without impacting the rocking action of the bolster or increasing its cost.

Bolster 50 is securely held in place on catheter 28 by removable plastic twist lock 80 which is closed about collar 51 to apply a gripping pressure on catheter 28 therein. Annular flanges 53 and 54 serve to hold twist lock 80 in place on collar 51. Twist lock 80 can be easily disengaged if the user desires to adjust the bolster or temporarily loosen it so that the surface underneath the bolster can be cleaned.

Bolster 50 is molded in one piece out of medical grade resilient silicone of about 50 shore A durometer, or a synthetic rubber such as Monsanto SANTOPRENE® or Shell Chemical KRATON®, which provides sufficient relative hardness so that the rocking action of bolster is maintained while being sufficiently flexibly resilient to supportively accommodate the flexing of catheter 28 therein. Top surface 52 is also molded flat to make for easy cleaning and nursing care.

Figure 3:
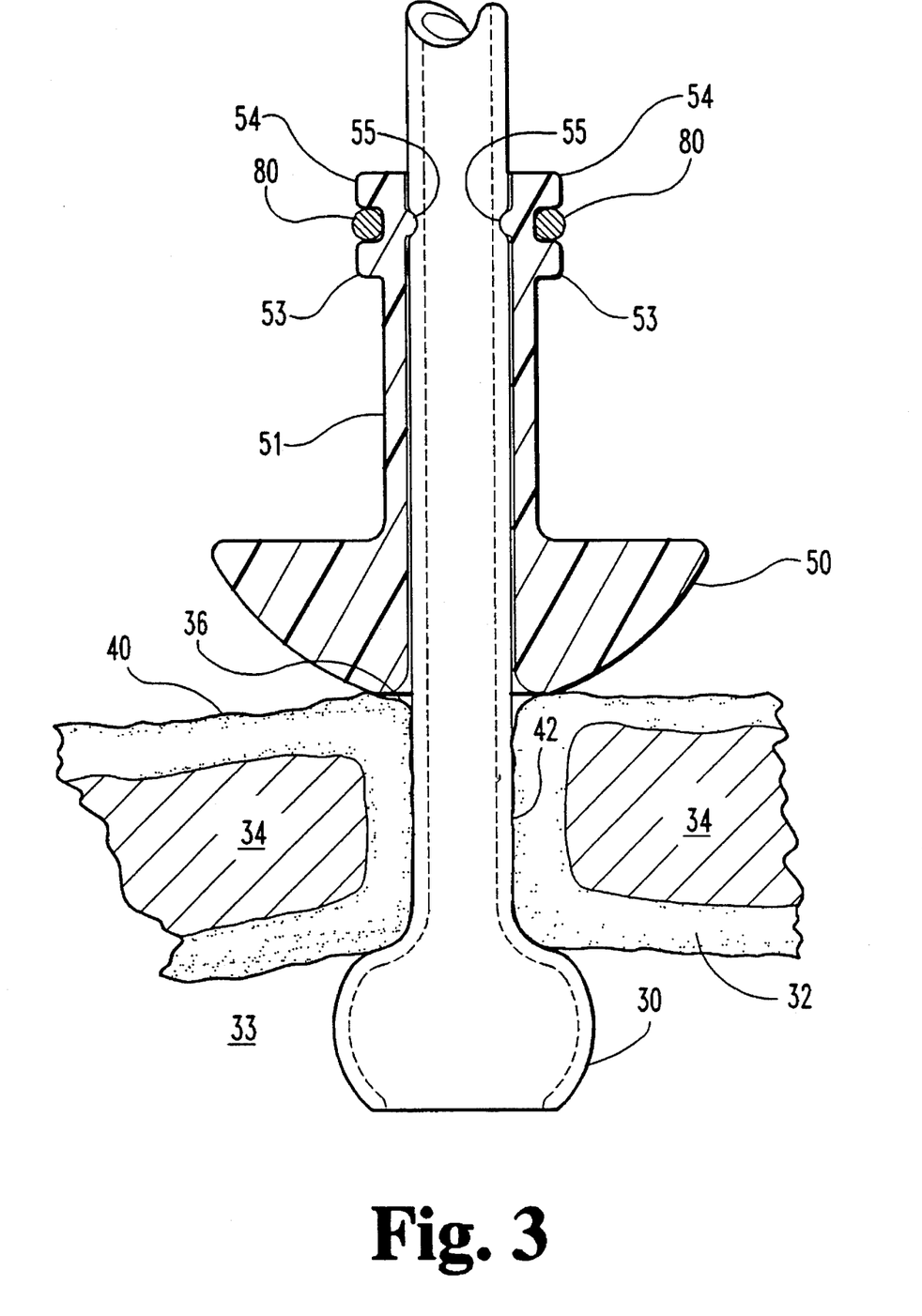
FIG. 3 is a side cross-sectional view of the bolster of FIG. 2 attached to a thin-walled catheter about a stoma site, with the catheter and bolster being shown in a non-flexed condition.
Figures 4A, 4B:
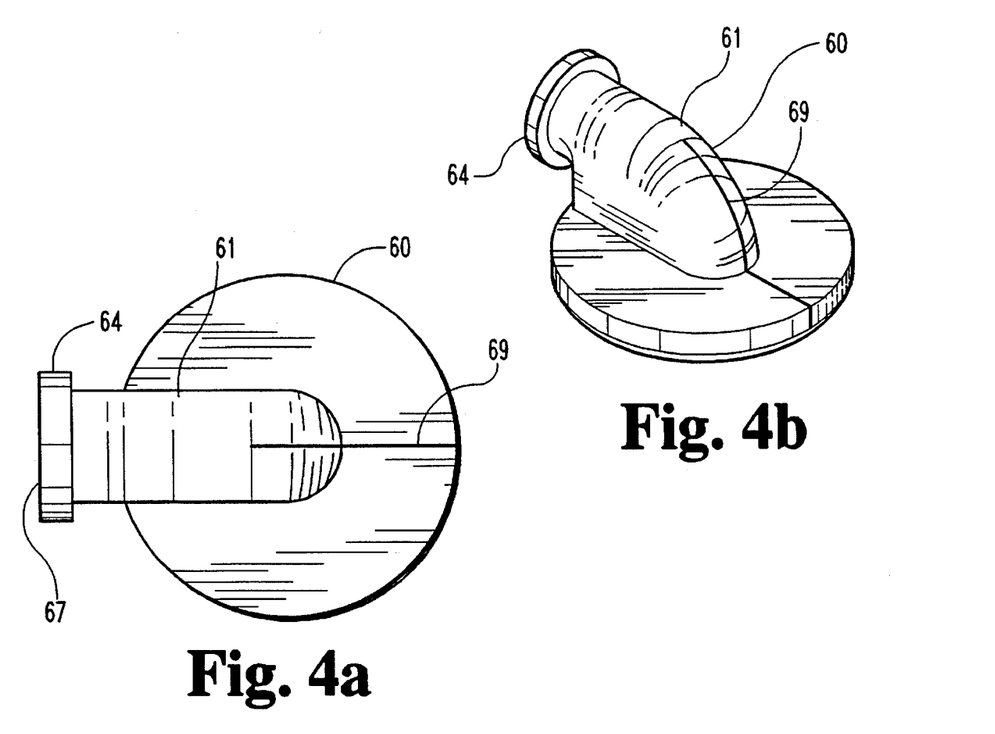
FIG. 4a is a top plan view of the side exit retention bolster.
FIG. 4b is a perspective view.
Figure 4C:
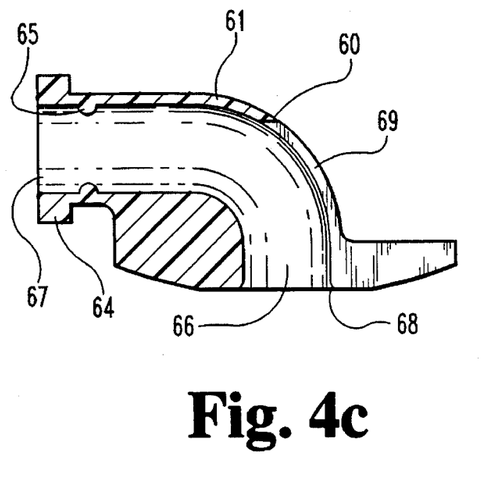
FIG. 4c is a side cross-sectional view.
Figure 4D:
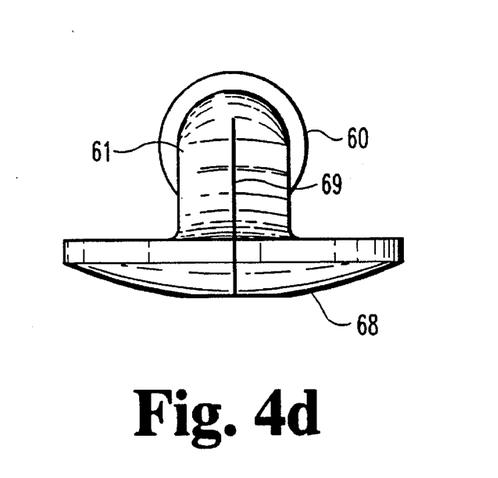
FIG. 4d is an end elevational view.

FIG. 3 is a side cross-sectional view of bolster 50 attached to thin-walled catheter 28 about stoma site 36 in a non-stressed condition, with catheter 28 and bolster 50 being shown in an up-right non-flexed condition about stoma site 36. FIG. 3 also shows reduced internal diameter portion 55, which applies pressure to catheter 28 to hold bolster 50 thereonto upon the application of plastic twist lock 80 thereabout.

FIGS. 4a–d are views of a side exit retention bolster 60. In FIGS. 4a–d, it is seen that bolster 60 defines a curved passageway 66 which opens to a side exit 67 on upstanding portion 61. Side exit bolster 60 also defines a slit 69 therethrough which is oppositely disposed from side exit 67 and through which catheter 28 can be passed to advance bolster 60 along catheter 28 and into position for mounting thereon. In other respects, the structure and functioning of bolster 60 are the same as for bolster 50, including convexly curved contacting portion 68 for rocking engagement when mounted at a stoma exit site, annular flange 64 for holding a twist lock in position, and reduced interior diameter portion 65 for applying pressure to a catheter to securely hold bolster in place thereon.

Figure 5:
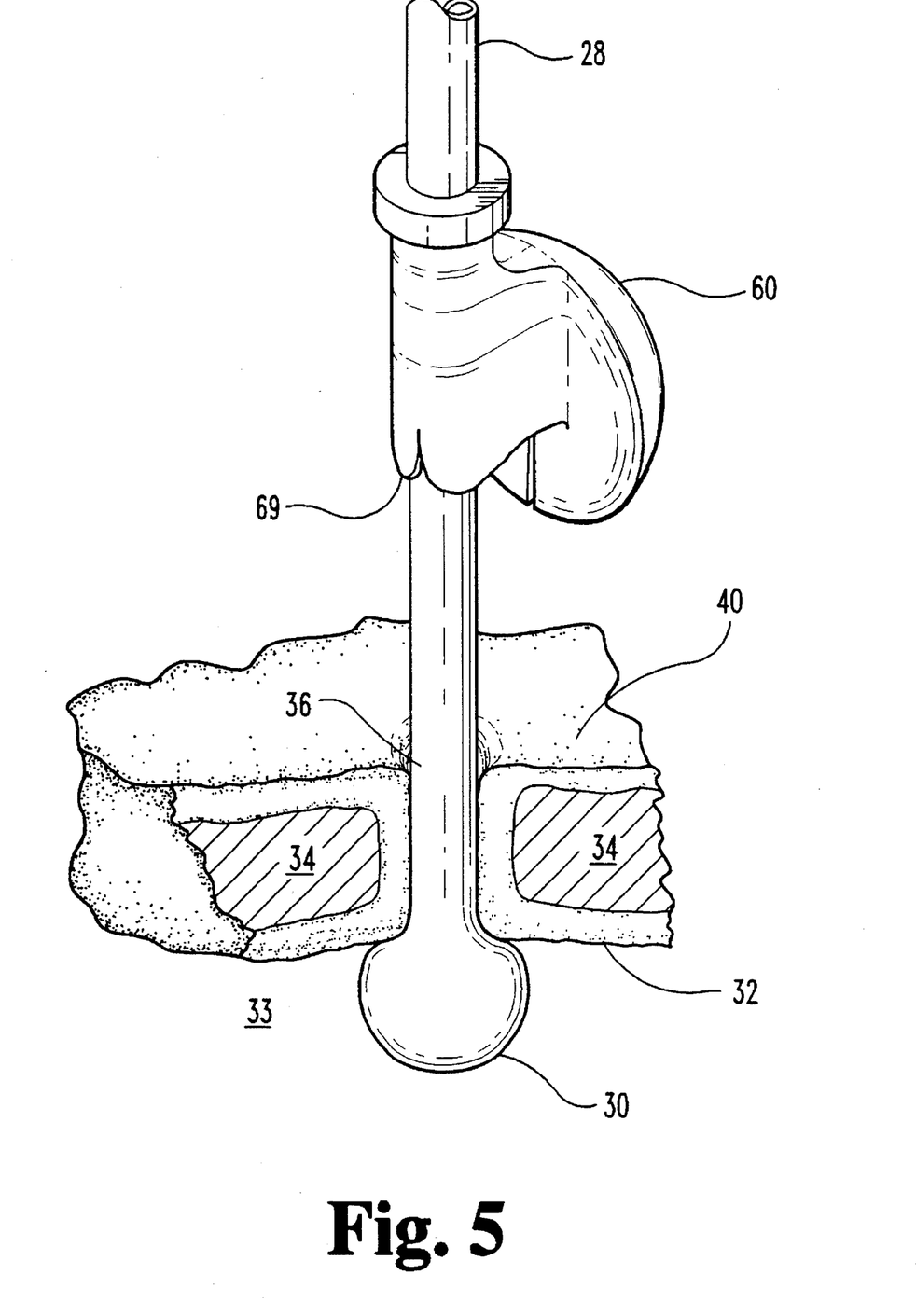
FIG. 5 is a perspective view of the side exit retention bolster of FIGS. 4a–d being advanced along a thin-walled catheter into position for mounting thereon.
Figure 6:
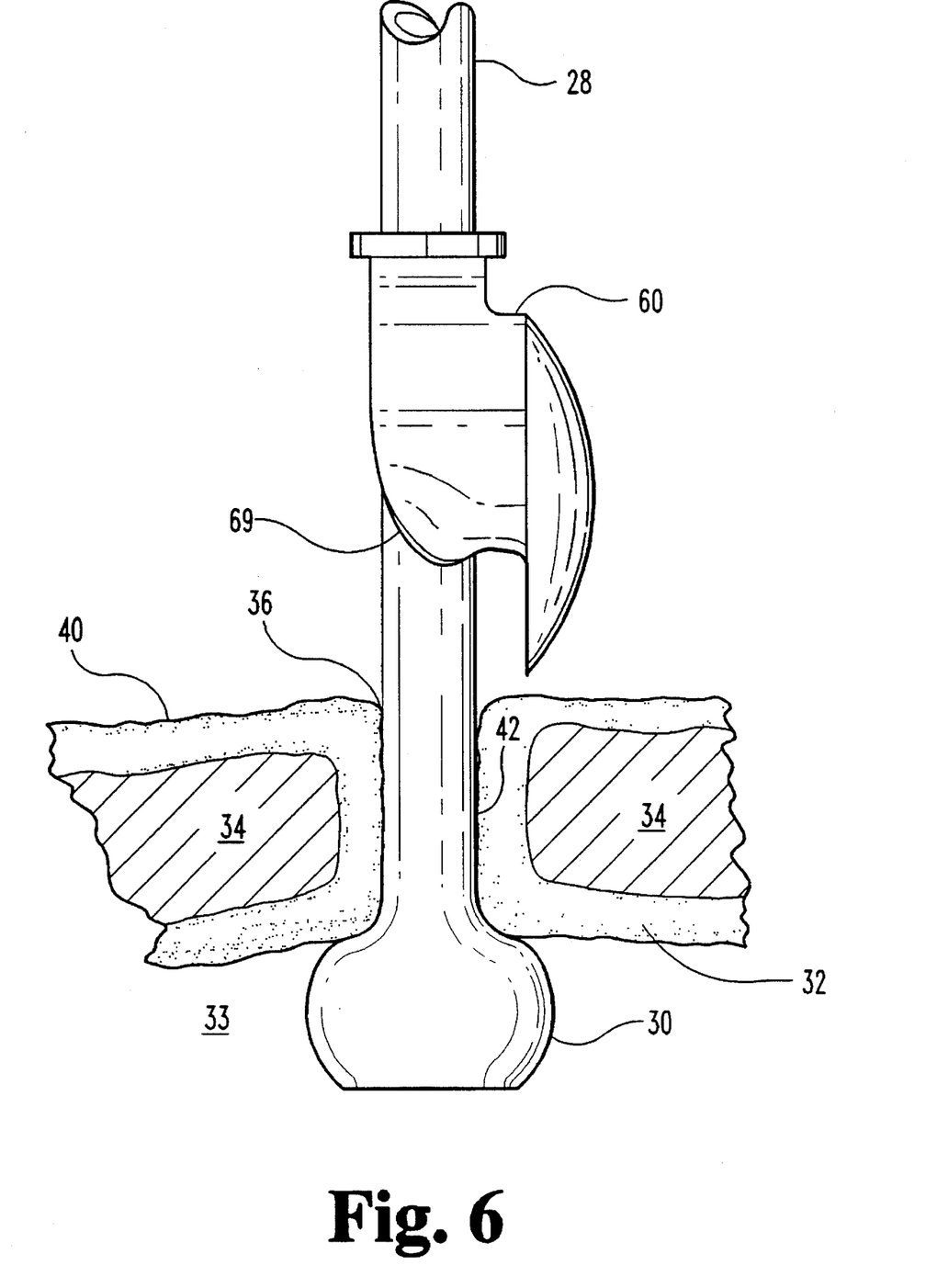
FIG. 6 is a side elevational view of the side exit retention bolster of FIGS. 4–5, shown advanced along the catheter and ready to be pivoted thereabout into a mounted position thereon.
Figure 7:
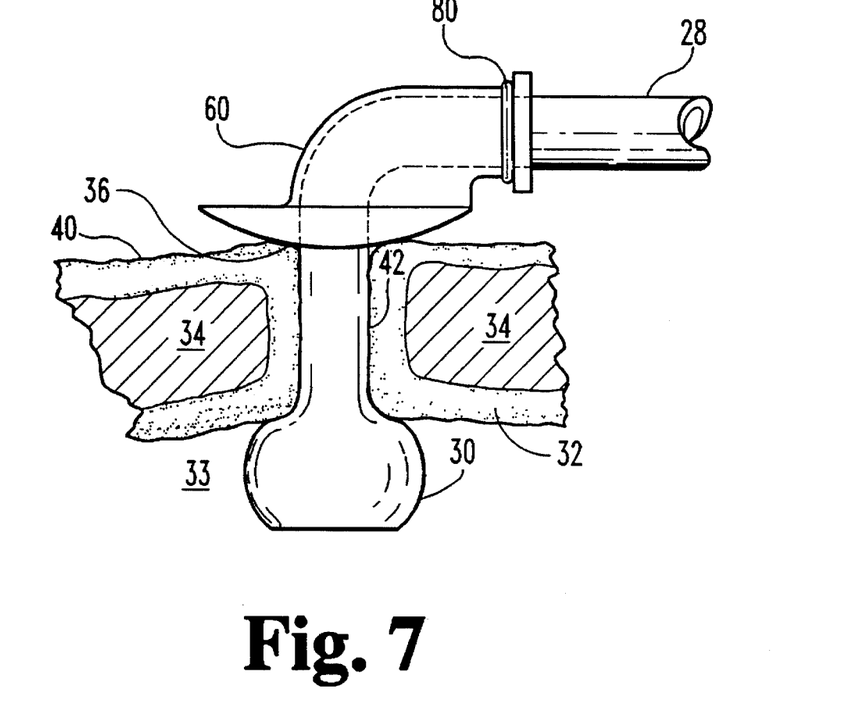
FIG. 7 is a side elevational view of the side exit rockable retention bolster of FIGS. 4–6, shown pivoted into position and mounted onto thin-walled catheter to retain the catheter at a stoma site.

FIG. 5 is a perspective view of side exit retention bolster 60 shown in the process of being advanced along thin-walled catheter 28 into position for mounting thereon at stoma site 36. As can be seen in FIG. 5, slit 69 is opened to allow passage of catheter 28 therethrough. In this way, bolster 60 can be easily advanced along catheter 28 and into position for mounting without having to bend and "force" advance catheter 28 through the curved portion of passageway 66. FIG. 6 is a side elevational view, which shows the advancement of bolster 60 along catheter 28 to be completed, with bolster 60 being ready to be pivoted into mounting arrangement. Bolster 60 is then pivoted to pass catheter 28 through slit 69 and fully into curved passageway 66. FIG. 7 shows bolster 60 after it has been so pivoted onto catheter 28 in mounting arrangement, and with twist lock 80 applied thereon to securely fasten bolster 60 to catheter 28. While the bending of catheter 28 within passageway 66, itself, may be sufficient to securely retain catheter 28 within passageway 66, the use of twist lock 80 on bolster 60 serves to provide added security against unintended migration.

The embodiment shown in FIGS. 4–7 provides the benefits of an upright rockable bolster, while also retaining catheter 28 at a fixed right angled orientation relative to stoma exit site. This configuration causes the proximal end of catheter 28 to be oriented substantially parallel with the skin surface 40, and thus establishes a very low profile. In this embodiment, the total height of the bolster above the skin surface can be constructed to be less than ⅞ inches high. Since catheter 28 is retained and fixed at a right angle, no kinking or repeated flexures of the catheter take place. This embodiment is especially useful when the catheter is used on active children.

Figure 8A:
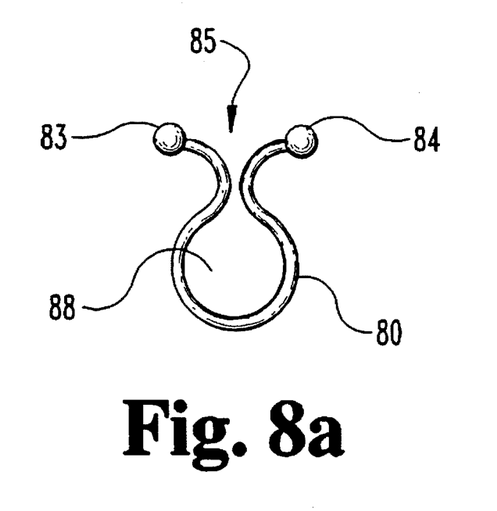
FIG. 8a is a top plan view of a plastic twist lock shown in an open condition.
Figure 8B:
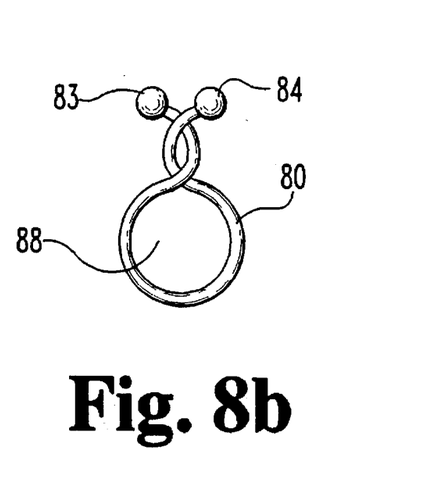
FIG. 8b is a top plan view of the plastic twist-lock of FIG. 8a, shown in a twist-lock closed condition.

FIG. 8a is a top plan view of an injection molded twist lock 80. Twist lock 80 is molded in polypropylene, with ball ends 83 and 84 which are used as finger grips to twist lock or unlock the device. The device is semi-rigid in that it is slid over the collar portions of any embodiment of the rockable bolsters through open entrance 85 which will flex open until circular opening 88 surrounds the collar of the bolster. FIG. 8b shows twist lock 80 closed wherein ball ends 83 and 84 are intertwined which twist locks the device closed. Twist locking the device closed compresses opening 88 to a smaller diameter which exerts a compression force on the collar on the bolster which in turn locks the catheter in place. Once the twist lock is engaged then the bolster securely locks onto the catheter.

If adjustment of the bolster is desired, then twist-lock 80 can be unlocked and the bolster pulled back to permit cleaning of the catheter body exit site. The bolster is then brought back down to the skin surface and twist lock 80 is re-engaged. The twist lock can be engaged or disengaged as often as desired. This twist lock mechanism permits repeated adjustments of the bolster to take place without having to cut a permanent locking pull tie and to get a new pull tie every time adjustment is needed. The twist lock shown will work on all collars of all embodiments of the pivotal bolster including the embodiments shown in the original application.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A retention bolster for retaining a tubular medical device against the epidermal surface at the exit site of the device from the body of a patient, said bolster comprising:

a main body having a convexly curved exterior surface portion for contacting the epidermal surface and an upstanding cylindrical portion extending therefrom; and means plural for securely attaching said main body to the tubular medical device including a longitudinal bore adapted for slidably receiving the tubular medical device therethrough, said longitudinal bore extending through said convexly curved exterior portion and said upstanding cylindrical portion, and means for securely retaining the tubular medical device within said longitudinal bore; wherein said main body is attachable to the tubular medical device with said convexly curved exterior portion in contact with the epidermal surface, and wherein said main body is rockable along contacting portions between said convexly curved exterior portion and the epidermal surface in response to movement of the tubular medical device about the exit site; and wherein said upstanding cylindrical portion is elongated and is resiliently flexible to thereby supportively allow the tubular medical device to be bent therein laterally away from said exit site without kinking.

2. The retention bolster of claim 1 in which said means for securely retaining the tubular medical device within said longitudinal bore includes a removable and reusable locking member which is positionable about said upstanding cylindrical portion and which is removably closeable thereabout to apply inward pressure upon a tubular medical device received within said longitudinal bore.

3. A retention bolster for retaining a tubular medical device against the epidermal surface at the exit site of the device from the body of a patient, said bolster comprising:

a main body having a convexly curved exterior surface portion for contacting the epidermal surface, and an upstanding portion extending therefrom, said upstanding portion defining a side opening; and means for securely attaching said main body to the tubular medical device including a passageway adapted for receiving the tubular medical device therethrough, said passageway extending through said convexly curved exterior portion and said upstanding portion to said side opening, and means for securely retaining the tubular medical device within said passageway; wherein said main body is attachable to the tubular medical device with said convexly curved exterior portion in contact with the epidermal surface, and wherein said main body is rockable along contacting portions between said convexly curved exterior portion and the epidermal surface in response to movement of the tubular medical device about the exit site; and wherein said passageway has a curved portion within said main body which curves towards said side opening to thereby bend and orient a tubular medical device therein toward and through said side opening and laterally away from the exit site of the device from the body without kinking.

4. The retention bolster of claim 3 in which said main body defines a slit therethrough which is oppositely disposed on said main body from said side opening, for allowing passage of a tubular medical device therethrough and into said passageway, wherein the advancement of said bolster along the tubular medical device may be facilitated by advancing the tubular medical device through said slit and out through said side opening, and wherein said bolster may be pivoted into a mounting arrangement on said tubular medical device by bending the tubular medical device through said slit and into said curved portion of said passageway.

5. A retention bolster for retaining a tubular medical device against the epidermal surface at the exit site of the device from the body of a patient, said bolster comprising:

a main body having an exterior surface portion for contacting the epidermal surface, and an upstanding portion extending therefrom, said upstanding portion defining a side opening; and means for securely attaching said main body to the tubular medical device including a passageway adapted for receiving the tubular medical device therethrough, said passageway extending through said exterior surface portion and said upstanding portion to said side opening, and means for securely retaining the tubular medical device within said passageway; wherein said main body is attachable to the tubular medical device with said exterior surface portion in contact with the epidermal surface; and wherein said passageway has a curved portion within said main body which curves towards said side opening to thereby bend and orient a tubular medical device therein toward and through said side opening and laterally away from the exit site of the device from the body without kinking, and wherein said main body defines a slit therethrough which is oppositely disposed on said main body from said side opening, said slit being resiliently openable to allow passage of a tubular medical device therethrough and into said passageway, wherein the advancement of said bolster along the tubular medical device may be facilitated by advancing the tubular medical device through said slit and out through said side opening, and wherein said bolster may be pivoted into a mounting arrangement on said tubular medical device by bending the tubular medical device through said slit and into said curved portion of said passageway.

* * * * *

UNITED STATES PATENT AND TRADEMARK OFFICE
CERTIFICATE OF CORRECTION

PATENT NO. : 5,484,420
DATED : January 16, 1996
INVENTOR(S) : Ronald D. Russo

It is certified that error appears in the above-indentified patent and that said Letters Patent is hereby corrected as shown below:

In column 6, line 45, please delete "means plural" and insert in lieu thereof --plural means--.

Signed and Sealed this

Eleventh Day of June, 1996

Attest:

BRUCE LEHMAN

Attesting Officer

Commissioner of Patents and Trademarks